United States Patent
Melles

(10) Patent No.: US 6,696,430 B1
(45) Date of Patent: Feb. 24, 2004

(54) USE OF VITAL DYE FOR FACILITATING SURGICAL PROCEDURES FOR VITREO-RETINAL SURGERY

(76) Inventor: Gerrit Reinold Jacob Melles, H.A. Maaskantstraat 31, NL-3071 MJ, Rotterdam (NL)

( * ) Notice: Subject to any disclaimer, the term of this patent is extended or adjusted under 35 U.S.C. 154(b) by 0 days.

(21) Appl. No.: 09/708,977

(22) Filed: Nov. 8, 2000

Related U.S. Application Data

(63) Continuation of application No. PCT/NL99/00283, filed on May 7, 1999.

(30) Foreign Application Priority Data

May 8, 1998 (EP) ............................................. 98201542
Aug. 17, 1998 (EP) ............................................. 98202751

(51) Int. Cl.[7] ........................ A61K 31/655; A61B 10/00
(52) U.S. Cl. ........................ 514/150; 514/150; 514/657; 514/728; 424/9.6; 424/9.61; 600/558; 604/28
(58) Field of Search ................................ 424/9.6, 9.61; 604/28; 600/558; 514/150, 657, 728

(56) References Cited

U.S. PATENT DOCUMENTS

| | | | | | |
|---|---|---|---|---|---|
| 4,350,676 A | * | 9/1982 | Laties et al. | .................... | 424/7 |
| 4,666,699 A | * | 5/1987 | Slifkin | ........................ | 424/7.1 |
| 6,024,719 A | * | 2/2000 | Morris | ........................ | 604/28 |
| 6,372,449 B1 | * | 4/2002 | Coroneo | .................... | 435/40.5 |

OTHER PUBLICATIONS

Dorland's Medical Dictionary. 1992 27th ed p. 1455.*
Atmaca et al., "La dêtection des nêovaisseaux sous–rêtiniens au moyen de la vidêo–angiographie au vert d'indocyanine," (with English abstract), *J. Fr. Ophthalmol.*, 20(3):189–194 (1997).
Liu et al., "Trypan Blue Staining on Retinal Ganglion Cell of Rat Insulted in Experimental High Intraocular Pressure," (abstract, No. XP–002082879), p. 1030, Dept. Neurobiology, University Changsha, Hunan, China (1992).
Saito, "Vital Staining of Retina and Uvea with Trypan Blue," (with English abstract), Dept. Ophthalmology, Jikei University School of Medicine, Tokyo, Japan, pp. 41–50 (1979).
Schmidt et al., "Ultrastructure of Trypan Blue Induced Ocular Defects: I. Retina and Lens," *Teratology*, 28:131–144 (1983).
Spector et al., "A Brief Photochemically Induced Oxidative Insult Causes Irreversible Lens Damage and Cataract I. Transparency and Epithelial Cell Layer," pp. 471–481 (1995).
Taniuchi, "Intraocular Penetration of Trypan Blue and of Colloidal Carbon Administered by IntraTenon's Capsulary Injection," (with English abstract) *Folia Ophthalmol*, (Dept. of Ophthalmol., Jikei Univ. School of Med., Tokyo, Japan) 32:343–350 (1981).

* cited by examiner

Primary Examiner—Russell Travers
Assistant Examiner—Shahnam Sharareh
(74) *Attorney, Agent, or Firm*—Banner & Witcoff, Ltd.

(57) ABSTRACT

A method for performing retinal membrane removal is disclosed using vital dyes which are applied to the membrane. Compositions including vital dyes which are useful in the retinal membrane removal methods are also disclosed.

9 Claims, No Drawings

USE OF VITAL DYE FOR FACILITATING SURGICAL PROCEDURES FOR VITREO-RETINAL SURGERY

This is a continuation application of international application No. PCT/NL99/00283, filed May 7, 1999; which claims priority from European patent application no. 98201542.2, filed May 8, 1998, and European patent application number 98202751.8, filed Aug. 17, 1998.

The invention relates to the field of ocular surgery, in particular to surgical procedures for vitreo-retinal surgery.

In the normal eye, the retina is located in the posterior segment of the eye, behind the corpus vitreum. The retina is a thin, translucent membrane resting on a single layer of pigmented epithelium, extending from the ora serrata to the optic disc. It consists of photoreceptor cells (rods and cones), which are connected to neuron pathways terminating in nonmyelinated fibers. These are combined to form the optic nerve. The innermost structure of the retina is the membrana limitans interna.

The vitreous is a clear, transparent, semi-solid gel which occupies about two thirds of the volume of the globe extending from the lens to the optic disc. It is a connective tissue space with the greater portion of the space made up of intercellular collagen and hyaluronic acid networks. The vitreous is in close contact with the epithelium of the pars plicata and pars plana, ora serrata and the internal limiting membrane of the retina as far as the optic disc. This contact may change with advancing years when the vitreous protein tends to shrink, and the vitreous detaches from the retina (=posterior vitreous detachment (PVD)).

The vitreous base represents the most solid attachment of the vitreous to the wall of the eye. It straddles the ora extending anteriorly on the pars plana over 1.5 to 2 mm and posteriorly on the retina over 3 to 4 mm. In PVD, the posterior vitreous separates from the retina and collapses anteriorly toward the vitreous base. Most retinal tears are caused by spontaneous or traumatic PVD, since traction on the vitreous here causes tenting of the retina and ciliary body. Retinal detachment may occur (sub)acutely. Virtually all retinal detachments could be repaired were it not for proliferative vitreoretinopathy (PVR) in which retinal pigment epithelial, glial, and other cells grow on both the inner and outer retinal surfaces and on the vitreous face to form a retinal membrane. These membranes may then contract, causing fixed folds, equatorial traction, detachment of the nonpigmented epithelium of the pars plana, and generalized retinal shrinkage. As a result, the causative retinal breaks may be reopened, or a traction detachment may develop. Hence, PVR is the most common cause of failure of retinal detachment surgery. Combining vitrectomy, scleral buckling, membrane peeling and dissection with extended retinal tamponade with long-acting gas ($C_3F_8$) or silicone oil enables about 75–90% of eyes undergoing vitrectomy for PVR to be eventually reattached, and about 50–75% to attain functional visual acuity of 5/200 or better. Eyes with PVR often require repeat procedures to reattach the retina such as fluid-gas exchange, laser photocoagulation, or reoperation.

Other retinal disorders in which membranes are formed include epiretinal membranes (macula Pucker), and macular holes, or a combination thereof. In the latter disorders, the macular function is compromised by gliose over the macula, that causes traction on the underlying retina, and therefore a distorted visual image for the patient. Both the PVR-membranes as well as the epiretinal membranes will be referred to as 'retinal membranes' in the text below.

Retinal membrane peeling and dissection is performed to relieve the traction on the retinal surface, so that the contracted tissue can be flattened out again. Removal of the membranes is often difficult, because the membranes consist of fibrous tissue having nearly the same color as the underlying retina. Improper visualization of the membranes on the retina therefore bears the risk of incomplete removal of the fibrous tissue, so that insufficient relaxation of the retina is achieved, or damage to the underlying retina, compromising its local function.

The present invention seeks to overcome the problems associated with poor visibility of the retinal membranes during vitreo-retinal surgery. It is an object of the invention to make it possible to visually distinguish the retinal membranes from the underlying retina, so that the membranes can be better identified during surgery, for example to prevent the uncomplete removal of the membranes, or damage to the retina itself.

Surprisingly, it has now been found that said object may be attained by using a specific dye or mixture of dyes, which is capable of staining tissue or a tissue component, such as a membrane, and which is physiologically and toxicologically acceptable. Hence, the invention relates to a method for performing retinal membrane removal, wherein the membranes are stained using at least one vital dye.

In a method according to the invention, the outer surface of the retinal membranes is selectively stained, by which is meant that the retinal tissue beneath the membranes is substantially not, or at least to a significantly lesser extent than the retinal membranes, stained. Accordingly, during the removal of the membranes, a clear distinction can be observed between the membranes that are being removed, and the underlying retina. This distinction facilitates the controlled removal of the membranes, and reduces the risk of inadvertent damage to the retina.

It has been observed that the staining of retinal. membranes does not have a detrimental effect on the tissue with which the dye is contacted. Furthermore, it has been observed that shortly after the surgical procedure has been completed, substantially all visible traces of the dye have disappeared. Thus, a patient undergoing vitreoretinal surgery involving staining of the retinal membranes in accordance with the invention experiences no more distress or undesired side effects as when a conventional surgical procedure, not involving staining, is employed.

Furthermore, undesired staining of the intraocular structures other than the retinal membranes does not, or not to an adverse extent, occur.

As has been mentioned above, in a method according to the invention, the retinal membranes are stained using a vital dye. A vital dye is a dye which has a sufficient coloring, or staining capacity at a concentration which is physiologically and toxicologically acceptable. In other words, the minimum amount of dye which is necessary to provide sufficient staining for a useful coloring to be visible should so be low that no, or hardly any, adverse toxic effects occur. Preferably, the dye is not or hardly toxic for the retina and adjacent structures. It is further preferred, that substantially no traces of the dye are present in the eye, shortly after the vitreoretinal procedure has been completed. As a result, there is hardly any risk of the patient experiencing any side-effects from the use of the dye.

Examples of suitable vital dyes include azafloxin, basic blue (nil blue sulphate), bismarck brown, basic red (rhodamine 6G), bengal red, brilliant crysyl blue, eosin, fluorescein, gentian violet, indocyanine green, janus green, methylene green, methylene blue, neutral red, trypan blue, and trypan red.

Particularly good results have been achieved using a vital dye which is capable of staining tissue or a tissue component, substantially without diffusing through said tissue. The word substantially indicates that, although care is taken that a suitable dye is selected, it is of course possible that the dye diffuses through tissue in very small amounts. It has been found, that in accordance with this embodiment a particularly clear distinction may be observed between the stained retinal membranes and the surrounding tissues, among which the retina. Furthermore, according to this embodiment, the risk that any substantial amounts of dye remain in the eye after the surgical procedure is decreased significantly.

Particularly suitable examples of vital dyes which are capable of staining tissue or a tissue component, substantially without diffusing through said tissue are dyes having the formula (I)

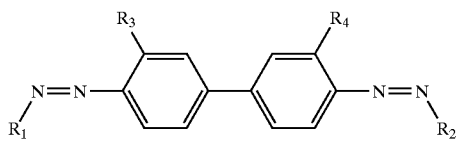

wherein $R_1$ and $R_2$ are the same or different arylgroups, and wherein $R_3$ and $R_4$ are independently chosen from hydrogen, methyl, ethyl, methoxy, amino, hydroxyl, and sulfonate. $R_1$ and $R_2$ are preferably the same and formed by substituted naphtylgroups. Preferably, the naphtylgroups are substituted with one or more of sulfonate groups, amino groups and hydroxyl groups. These dyes have been found to bind predominantly to fibrous tissue, such as the tissue of the retinal membranes, in the circumstances that are envisaged for application of the present invention.

In a highly preferred embodiment, the dye is chosen from the group of trypan blue, trypan red, brilliant crysyl blue, and indocyanine green. It has been found that these dyes provide a clearly visible staining at very low amounts. Also, they have an extremely advantageous toxicity profile. More preferably, the dye is trypan blue.

Of course it is also possible to use mixtures of the above dyes as long as the resulting mixture is capable of achieving a color of retinal membranes which can be easily distinguished from the color of the material below or adjacent to said membranes.

The dye is preferably used as a physiologically compatible solution. In a particularly preferred embodiment, the dye is formulated in an aqueous salt solution, which is isotone with ocular fluid. The salt is preferably sodium chloride, sodium phosphate, potassium chloride, calcium chloride, magnesium chloride, or a combination thereof. Suitable examples are Balanced salt solution or Hartmann's lactated Ringer's solution (Nuijts RMMA, Edelhauser HF, Holley GP, "Intraocular irrigating solutions: a comparison of Hartmann's lactated Ringer's solution, BSS and BSS plus", Clin. Exp. Ophtamol., vol. 233 (1995), pp. 655–661). In accordance with this embodiment, the salt concentration will be in the range of 0.8 to 1.0 wt. %, based on the weight of the solution.

It is further preferred that the solution has a neutral pH, i.e. a pH between 6.5 and 7.5. The skilled person will be able to select a suitable buffer, which has the properties to be of use in opthtalmic applications. An example of a suitable buffer is phosphate buffered NaCl, commercially available at NPBI, Emmer-Compascuum, The Netherlands.

In certain cases, depending on the desired manner of applying the dye solution to the retinal membranes, it may be desired to formulate said solution as a dispersion, or a viscous or viscoelastomeric solution, for example using hyaluronic acid (see WO-A-96/32929). In certain cases, a higher viscosity may be desired in order to achieve better adherence of the dye to the retinal membranes. It will be well within the standard expertise of the skilled person to select a suitable form for the solution.

The concentration of the dye or the mixture of dyes in the solution will preferably be between 0.01 and 3 wt. %, more preferably between 0.05 and 0.5 wt. %, based on the weight of the solution. Within this range, the concentration may be adapted to the toxicity and coloring characteristics of the dye used. It is preferred that such an amount is chosen that an optimal staining effect is achieved, while at the same time the risk of possible damage to the eye or any part thereof due to the toxicity of the dye is minimized.

A method according to the invention is preferably employed as part of a vitreo-retinal surgical procedure. Such a surgical procedure may for instance be based on one of the following techniques: retinal detachment surgery, macula Pucker removal, or macular hole surgery. Preferably, the surgical procedure is performed on a mammalian eye, more preferably on a human eye.

After the eye is opened, for example by making a scleral incision, the vitreous (ocular gel) is removed and the posterior segment of the eye is filled with air. A few drops of the above described solution comprising the dye in an appropriate concentration is applied onto the retinal membranes. The application of the solution may be carried out by bringing a canula that is attached to a syringe containing the dye onto the vitreous cavity, and to inject a few drops of the dye, generally less than 1 ml, onto the retinal membranes.

The vitreous cavity is filled with air, so that the concentration of the dye in the solution is not lowered by liquid vitreous, and the dye can be applied onto a specific retinal area. As an alternative the dye can be administered in a higher concentration into the liquefied vitreous, or a dispersion of the dye in a viscous or viscoelastomeric solution can be used.

Preferably, excess of dye is washed out by irrigating the vitreous cavity, leaving a faint but clear staining of the retinal membranes, after which the surgery can be continued using routine techniques. The irrigation may be carried out by using Balanced salt solution or any other solution that is commonly used in intraocular surgical procedures.

After the retinal membranes have been stained, the membranes can be removed using routine surgical techniques. Although care should be taken that as much of the retinal membranes as possible is removed, it will be clear that the invention also encompasses surgical procedures wherein small parts of the retinal membranes are unintentionally not removed and remain present after the surgery. The retinal membranes can be identified because of the difference in color between the stained retinal membranes and the non-staining underlying retina, so that the outline of a retinal membrane can be visualized during its removal.

The invention will now be elucidated by the following, non-restrictive examples.

EXAMPLE I 1 g of Trypan blue powder (Gurr, BDH Laboratory Supplies, Poole, United Kingdom) was dissolved in 1000 ml (1 liter) of Balanced salt solution (an aqueous solution of 0.9% NaCl) to obtain a concentration of 0.1 wt. % dye in solution. From the solution, 0.5 ml was drawn into a syringe, and a canula was attached to the syringe.

EXAMPLE II

In-vivo vitreo-retinal procedures were carried out on human eyes. A scleral incision was made, the vitreous was removed and the vitreous cavity was filled with air. A brush with some dye, oi a canula that was attached to a syringe containing the dye solution prepared in accordance with Example I was brought into the vitreous cavity. The tip of brush or the canula was held against an area with a retinal membrane(s), and a small amount of the dye in solution was applied onto the retinal membrane(s). Then, the vitreous cavity was flushed with Balanced salt solution (without dye), until all visible traces of the dye were washed out. A bluish staining of the retinal membrane(s) was visible, with fibrillar staining of the fibrous tissue.

The retinal membrane(s) was then removed using routine surgical techniques, for example 'membrane peeling' or 'epiretinal membrane removal'. The removal of the membranes was controlled by visualization of the blue stained membrane(s), whereas the surrounding or underlying retina was seen as gray tissue adjacent to the membrane or in the area where the membrane(s) had been removed.

After completion of the retinal membrane removal, the vitreo-retinal procedure was completed as in routine procedures.

What is claimed is:

1. A method of removing a retinal disorder membrane from an inner surface of a retina comprising the steps of:

surgically opening an eye;

applying a vital dye onto the retinal disorder membrane located at an inner surface of the retina relative to vitreous to produce a stained retinal disorder membrane such that the retinal disorder membrane is stained without substantially staining internal limiting membrane of the retina or retinal layers underlying the internal limiting membrane compared to the stained retinal disorder membrane; and surgically removing the stained retinal disorder membrane from the inner surface of the retina.

2. A method according to claim 1, wherein the retinal disorder membrane is formed by proliferative vitreoretinopathy.

3. A method according to claim 1, wherein the retinal disorder membrane is an epiretinal membrane.

4. A method according to claim 1, wherein the method is part of a vitreo-retinal surgical procedure.

5. A method according to claim 1, wherein the dye is capable of staining tissue without substantially diffusing through said tissue.

6. The method according to claim 1, wherein the vital dye is selected from the group consisting of trypan blue, trypan red, brilliant crysyl blue, and indocyanine green.

7. The method according to claim 1, wherein the vital dye is present in a physiologically compatible solution in a concentration between 0.01% and 3% by weight.

8. The method according to claim 7, wherein the physiologically compatible solution comprises salt between 0.8% and 1.0% by weight.

9. The method according to claim 8, wherein the salt is selected from the group consisting of sodium chloride, sodium phosphate, potassium chloride, calcium chloride, and magnesium chloride.

* * * * *